US008670897B1

(12) United States Patent
Ralson

(10) Patent No.: US 8,670,897 B1
(45) Date of Patent: Mar. 11, 2014

(54) MOBILE IN-VEHICLE COMMUNICATION AND ROUTING APPARATUS, SYSTEM, AND METHOD

(75) Inventor: Robert E. Ralson, Eugene, OR (US)

(73) Assignee: Feeney Wireless, LLC, Eugene, OR (US)

(*) Notice: Subject to any disclaimer, the term of this patent is extended or adjusted under 35 U.S.C. 154(b) by 538 days.

(21) Appl. No.: 12/956,293

(22) Filed: Nov. 30, 2010

Related U.S. Application Data

(60) Provisional application No. 61/266,100, filed on Dec. 2, 2009.

(51) Int. Cl.
G06F 7/00 (2006.01)
G06F 17/00 (2006.01)
G01M 17/00 (2006.01)
G06F 11/30 (2006.01)
G06F 19/00 (2011.01)
G07C 5/00 (2006.01)

(52) U.S. Cl.
USPC ............. 701/36; 701/45; 701/48; 701/29.1; 701/31.4; 701/31.5; 701/32.3; 701/32.4; 701/33.2; 701/33.4; 701/408; 701/517

(58) Field of Classification Search
None
See application file for complete search history.

(56) References Cited

U.S. PATENT DOCUMENTS

| 5,132,666 | A | | 7/1992 | Fahs |
|---|---|---|---|---|
| 5,949,776 | A | * | 9/1999 | Mahany et al. ............... 370/338 |
| 6,028,537 | A | * | 2/2000 | Suman et al. ................. 340/988 |
| 6,060,993 | A | | 5/2000 | Cohen |
| 6,078,566 | A | | 6/2000 | Kikinis |
| 6,392,531 | B1 | * | 5/2002 | Gabbard ....................... 340/5.31 |
| 6,433,706 | B1 | | 8/2002 | Anderson, III et al. |
| 6,580,981 | B1 | | 6/2003 | Masood et al. |
| 6,611,201 | B1 | * | 8/2003 | Bishop et al. ............ 340/426.21 |
| 6,831,556 | B1 | | 12/2004 | Boykin |
| 7,149,197 | B2 | | 12/2006 | Garahi et al. |
| 7,323,970 | B1 | * | 1/2008 | Murray et al. ........... 340/426.12 |
| 2004/0127206 | A1 | * | 7/2004 | Van Bosch et al. ........... 455/418 |
| 2005/0090940 | A1 | * | 4/2005 | Pajakowski et al. .............. 701/1 |
| 2005/0192727 | A1 | * | 9/2005 | Shostak et al. .................. 701/37 |

(Continued)

OTHER PUBLICATIONS

Transceiver_ComputerUserDict.pdf (Dictionary—transceiver—, 5/211/2013, http://www.computeruser.com/dictionary/, pp. 1-2).*

(Continued)

Primary Examiner — Khoi Tran
Assistant Examiner — Bao Long T Nguyen
(74) Attorney, Agent, or Firm — David A. Crowther

(57) ABSTRACT

An in-vehicle mobile communication and routing apparatus for use with a taxi cab, public safety vehicle, delivery truck, fire truck, emergency vehicle, or any vehicle. Embodiments of the invention include a system incorporating the apparatus and a method for using the same. The mobile apparatus is attachable to a vehicle and includes a plurality of long-range transceivers communicatively coupled with one or more databases located remotely from the vehicle, and a plurality of short-range transceivers communicatively coupled with one or more devices external to the mobile apparatus and proximally located to the vehicle. An intelligent power supply is structured to monitor a battery condition of the vehicle and initiate a controlled shutdown of the mobile apparatus responsive to at least one of a timer countdown and a voltage threshold of a vehicle battery. Devices external to the mobile apparatus communicate with an in-vehicle processor and one or more remote databases.

32 Claims, 5 Drawing Sheets

(56) References Cited

U.S. PATENT DOCUMENTS

| | | | |
|---|---|---|---|
| 2005/0243867 A1* | 11/2005 | Petite | 370/474 |
| 2006/0109107 A1* | 5/2006 | Staton et al. | 340/539.13 |
| 2006/0217864 A1* | 9/2006 | Johnson et al. | 701/45 |
| 2006/0271246 A1* | 11/2006 | Bell et al. | 701/1 |
| 2008/0177436 A1* | 7/2008 | Fortson | 701/29 |
| 2009/0119013 A1* | 5/2009 | O'Malley | 701/211 |

OTHER PUBLICATIONS

PortDefinition (port—definition of port by the Free Online Dictionary, Thesaurus and Encyclopedia., May 28, 2013, http://www.thefreedictionary.com/port, pp. 1-6).*

* cited by examiner

MOBILE IN-VEHICLE COMMUNICATION AND ROUTING APPARATUS, SYSTEM, AND METHOD

CROSS REFERENCE TO RELATED APPLICATION

This application claims the benefit of U.S. Ser. No. 61/266,100, filed Dec. 2, 2009, herein incorporated by reference.

FIELD OF THE INVENTION

This application pertains to a mobile in-vehicle device, and more particularly, to a mobile communication and routing apparatus configurable within a vehicle, a system incorporating the apparatus, and method for using the same.

BACKGROUND

As the sophistication of taxi cabs, public safety vehicles, delivery trucks, fire trucks, emergency vehicles, and the like, continues to expand, so too does the need for more sophisticated mobile communication devices. For example, taxi-cab drivers have needs for communicating with central offices, remote databases, payment services, or other tracking databases. Police officers have myriad needs for communicating with other police officers, central command offices, or with criminal tracking databases, among other needs. Emergency personnel have needs for collecting medical or health diagnostics information, and quickly processing or communicating such information to others. Trucking or delivery companies have needs for monitoring or dispatching fleets of vehicles. Some vehicles have needs to communicate and process information from passengers or other people within the vehicle or in the near vicinity. Automation is an important aspect of processing such information because a driver must be able to concentrate on the road, or other tasks at hand, without compromising the quality or reliability of the communications.

Moreover, physical space within a vehicle is limited and commands a premium. Conventional approaches require the use of bulky and cumbersome devices, which consume valuable vehicle space. Attempts to provide reliable and effective in-vehicle communication devices and services have resulted in frustration, loss of revenue, and in the extreme cases, loss of life. Some approaches include using multiple separate devices that are networked in a "science project" fashion, which often fail to reliably interoperate one with another. Such approaches can lead to drained car batteries, particularly after the vehicle has been shutdown, or otherwise cause unintended shorts, hardware or software crashes, and other problems.

Standard communication systems are limited in their ability to communicate in difficult-to-reach communication areas. Such systems and devices also lack the ability to effectively provide short-range communication or computing services, and bridge the services together in a cohesive, automated, and compact device. While there have been a number of systems directed toward assisting in vehicle-related communications, there remains a need for a versatile, compact, and user-friendly apparatus and system, which can assist taxi-cab drivers, law enforcement, emergency personnel, trucking companies, delivery companies, and the like, in easily communicating between vehicles and remote command centers, or monitoring fleets of vehicles.

There also remains a need for assisting persons or devices that are within the vehicle, or proximally located to the vehicle, with communicating or processing needs. There is a particular need for an apparatus that supports both wired and wireless communication ports for various devices for use by persons within the vehicle or located about the vehicle. There is also a need for an apparatus that can interface with external devices to connect and transmit information and data. There also remains a need for a mobile in-vehicle apparatus that can automatically monitor the conditions of the vehicle battery and otherwise safe-guard the mobile apparatus and the vehicle battery.

Accordingly, needs remain for an improved mobile in-vehicle communication and routing apparatus, system, and method.

The foregoing and other features of the invention will become more readily apparent from the following detailed description, which proceeds with reference to the accompanying drawings.

DETAILED DESCRIPTION OF THE EMBODIMENTS

Figure 1:
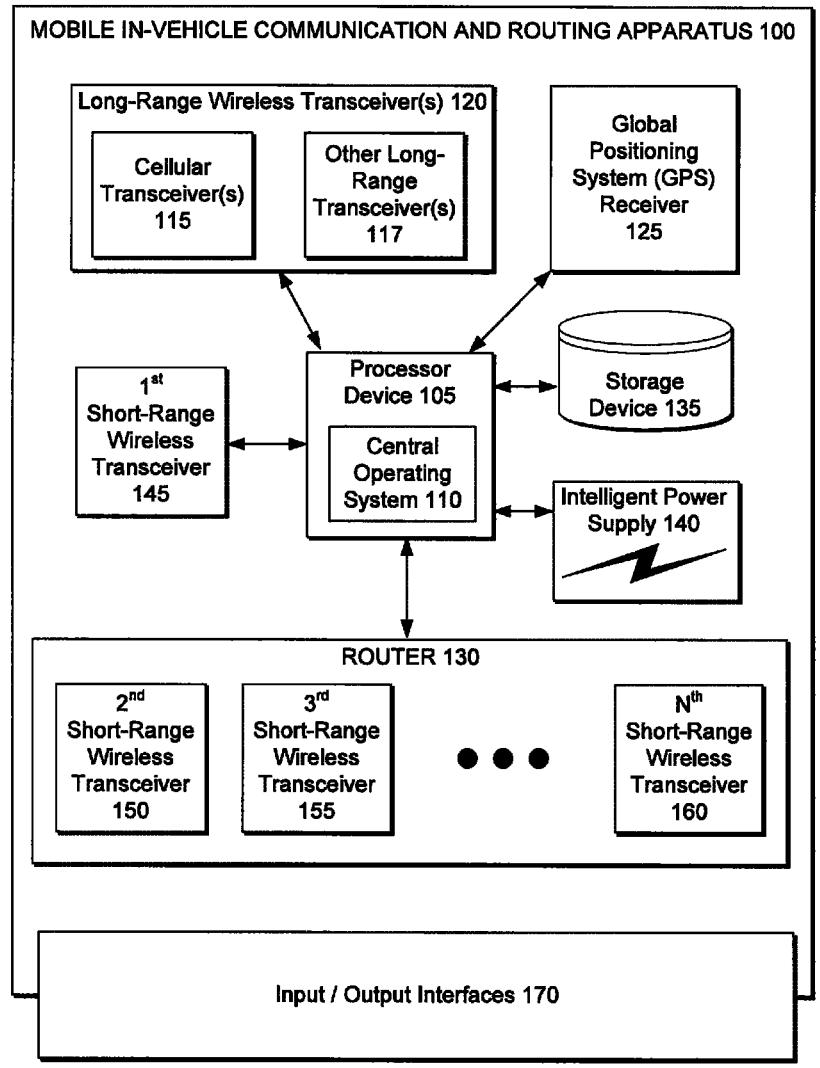
FIG. 1 shows a block diagram of an example embodiment of a mobile in-vehicle communication and routing apparatus.

FIG. 1 shows a block diagram of an example embodiment of a mobile in-vehicle communication and routing apparatus 100. Although the term "in-vehicle" is generally used herein, it should be understood that the mobile apparatus 100 can be located in a compartment atop a vehicle (not shown), or about the vehicle, and need not necessarily be physically located inside the vehicle. The mobile apparatus 100 provides a unified communications gateway for one or more users, who may be located in or about the vehicle.

The mobile apparatus 100 includes a processor device 105 for controlling the mobile apparatus 100 and the various components included therein, and for providing real-time onboard processing of vehicle data. The mobile apparatus 100 also includes long-range transceivers 120, a global positioning system (GPS) receiver 125, short-range transceivers 145, 150, 155, and 160, an intelligent power supply 140, and a storage device 135. Some or all of the components of the mobile apparatus 100 can be integrated on a single board, or alternatively, some or all of the components may be incorporated on separate boards. Some components may be separate devices included within the same enclosure as the other boards or components and operatively associated therewith. The storage device 135 may include a hard disk drive (HDD), optical disk drive, non-volatile memory such as flash memory chip, and/or other suitable storage device. User applications or other data can be loaded onto the mobile apparatus 100, or otherwise stored on the storage device 135. Such applications can include, for example, Computer Aided Dispatch (CAD), vehicle navigation, automatic vehicle location (AVL), vehicle on-board diagnostics and/or telematics, remote database access, virtual private networking (VPN), World Wide Web/Internet access, voice over Internet protocol (VoIP), and/or video conferencing, among other suitable applications.

The processor device 105 operates the central operating system 110, which coordinates the operation of the hardware components of the mobile apparatus 100, and manages the flow of information between the various components and/or the users. The operating system 110 can include, for example, a Windows® or Linux® operating system, among other suitable operating systems. The processor device 105 includes any hardware, such as Application Specific Integrated Circuits (ASICs), Field Programmable Gate Arrays (FPGAs), Digital Signal Processors (DSPs) or microprocessors, software such as specially generated programs or codes structured to operate in conjunction with the hardware listed above, firmware, or any combination thereof for controlling the components of the mobile in-vehicle communication and routing apparatus 100.

Geographic positioning information can be received by the Global Positioning System (GPS) receiver 125 included in the mobile apparatus 100. For example, the positioning information can indicate a position or location of the mobile apparatus 100, and therefore the vehicle. The processor device 105 can configure operating parameters of the GPS receiver 125 and receive the positioning information from the GPS receiver 125. The positioning information can then be transmitted by the processor device 105 to users interfacing with the mobile apparatus 100, or otherwise stored in storage device 135. In addition, the positioning information can be transmitted to a remote server or database via one or more long-range wireless transceivers 120. This "store and forward" process reduces the chance of loss of the geographic positioning information and maintains high availability of the historic geographic positioning information to the mobile apparatus 100 even in the event of a network failure or outage.

In addition, the GPS information can be associated in time with any of the other transmissions described herein, and in such manner, geographic descriptive information can be associated with any transmission of information described herein. For instance, when the positioning information is received by the processor device 105, the positioning information can be timestamped. In addition, the positioning information and the associated timestamp can be stored and/or transmitted to a remote database or server with any other information, such as camera images, medical information, health information, vehicle information, user information, luggage information, package information, and so forth, including any of the information disclosed in further detail below.

The long-range wireless transceivers 120 can include, for example, third generation (3G) or fourth generation (4G) cellular transceivers 115, satellite transceivers, and/or other suitable long-range wireless transceivers 117. The long-range transceivers 120 are generally associated with a network. For example, the cellular transceivers 115 are operatively associated with a cellular network. The term "cellular network" is herein defined as a radio network including one or more cells to provide radio coverage to a wider area than any one given cell.

Cellular networks may be built using a variety of standards. The most common standards in use today include frequency division multiple access (FDMA), code division multiple access (CDMA), or Global System for Mobile (GSM) communications standards, but the embodiments of the present invention are not limited thereto. One or more of the long-range transceivers 120 may be associated with a Worldwide Interoperability for Microwave Access (WiMAX®) network, or other suitable networks. The processor device 105 controls the long-range wireless transceivers 120 and can transmit information to the transceivers 120 or receive information, process, and store the information in the storage device 135. The long-range transceivers 120 can support the Internet Protocol (IP) for data connectivity between the mobile device 130 and the remote towers or databases, among other suitable protocols.

The term "long-range" is used herein to generally refer to transceivers or devices which are structured to transmit and receive information to and from remote points significantly distant from the vehicle, such as remote towers or databases. The long-range transceivers 120 provide a longer range than short-range wireless transceivers or devices, which are used for connecting users or devices within or proximally located about the vehicle to the mobile apparatus 100.

The mobile apparatus 100 also includes 1st through Nth short-range transceivers, such as short-range transceivers 145, 150, 155, and 160 shown in FIG. 1. For example, short range transceiver 145 may include a Bluetooth® transceiver for operatively coupling the mobile apparatus 100 to users or devices located close to the vehicle. Further, a router 130 includes short-range wireless transceivers 150, 155, and 160, which may be associated with, for example, a wireless local area network (WLAN), or WI-FI® network, among other suitable networks. The router 130 can operate as an access point for multiple users or external devices, or as client station(s) in an ad-hoc network.

Input and/or output interfaces 170 provide interface connections to a variety of external devices, which may be operatively associated with the mobile apparatus 100. The term "external devices" is generally used herein to refer to devices that are external to the mobile apparatus 100, although such devices may be internal or external to the vehicle itself. The input and/or output interfaces 170 may include wired interfaces. Alternatively, or in addition to the wired interfaces, the input and/or output interfaces 170 may include wireless interfaces, which may be associated with the router 130 or the short-range wireless transceiver 145. The input and/or output interfaces 170 can support the Internet Protocol (IP) for data connectivity, among other suitable protocols. Moreover, Hypertext Transfer Protocol (HTTP), secure HTTP (HTTPS), secure shell (SSH), and/or Telnet interfaces may be supported by or otherwise operated over the input and/or output interfaces 170.

Figure 2:
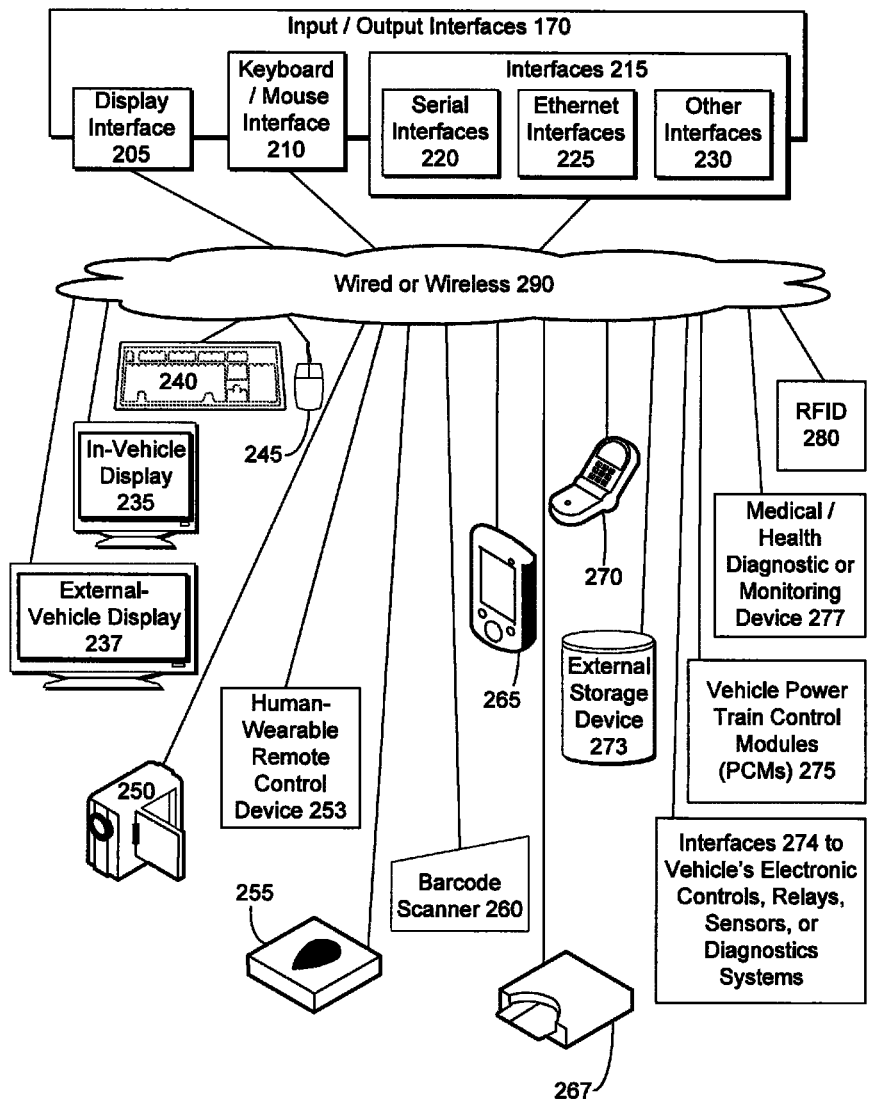
FIG. 2 shows additional aspects of the input and/or output interfaces of the mobile in-vehicle communication and routing apparatus of FIG. 1, and various components operatively associated therewith.

FIG. 2 shows additional aspects of the input and/or output interfaces 170 of the mobile in-vehicle communication and routing apparatus of FIG. 1, and various components operatively associated therewith. The input and/or output interfaces 170 may include a display interface 205 for operatively coupling an in-vehicle display 235 and/or an external-vehicle display 237 to the mobile apparatus 100. The external-vehicle display 237 may be located, for example, atop the vehicle and may be configured to provide digital signage, display advertisements, and/or other information, to individuals around the vehicle. The in-vehicle display 235 is located in the vehicle and can provide a graphical user interface for one or more users to interact with or configure the mobile apparatus 100. A keyboard 240 and mouse 245 may be operatively coupled to the keyboard interface and/or mouse interface 210 to allow one or more users to control or otherwise interact with the mobile apparatus 100. The display interface 205 and the keyboard and/or mouse interface 210 may include wired or wireless interfaces.

The mobile in-vehicle communication and routing apparatus 100 provides interfaces for a variety of devices, which may be operatively coupled to the apparatus 100 via interfaces 215. The interfaces 215 can include serial interfaces 220, Ethernet interfaces 225, and/or other suitable interfaces 230. The interfaces 215 may be associated with the short-range wireless transceivers such as 145, 150, 155, and 160 of FIG. 1, or alternatively, may include wired interfaces. The interfaces 215 are structured to communicate with external devices, for example, a camera 250, a human-wearable remote control device 253, a biometric device 255, a barcode scanner 260, a personal digital assistant (PDA) 265, a smart card interface 267, a mobile telephone 270, an external storage device 273, vehicle power train control modules 275, medical and/or health diagnostic or monitoring device 277, interfaces to the vehicle's electronic controls, relays, sensors, or diagnostics Systems 274, and/or a Radio Frequency Identification (RFID) device 280. Any of the external devices may be operatively coupled to the mobile in-vehicle communication and routing apparatus 100 via a wired or wireless path 290.

Serial interfaces 220 may include, for example, Universal Serial Bus (USB), RS-232, or RS-485 interfaces, among other suitable serial interfaces. Ethernet interfaces 225 may provide RJ45 connectors for operatively coupling external devices to the mobile apparatus 100. Further, other interfaces 230 may be used, which may be operatively associated with the short-range transceivers 145, 150, 155, or 160, as shown in FIG. 1. The interfaces 215 may also be used to configure different operating parameters or modes of the mobile device 100.

The external devices may be operatively coupled to the mobile in-vehicle communication and routing apparatus 100 using any one of the interfaces 170, and provide various types of application interfaces or other services to one or more users within the vehicle or located about the vehicle. For example, a human-wearable remote control device 253 may be operatively coupled to the mobile apparatus 100 using short-range wireless transceiver 145. The human-wearable remote control device 253 can be worn by a law enforcement officer to send out a mayday or other distress signal to the processor device 105 of the mobile apparatus 100 via the short-range wireless transceiver 145, which may then be relayed to a central command center via one or more long-range wireless transceivers 120. The remote control device 253 can also turn on or off a siren associated with the vehicle, remotely operate lights or other parts of the vehicle, remotely operate the ignition system, vehicle air-conditioner or heating system, and so forth. Other devices such as still-image or video-cameras attached to the vehicle can be operated using the wearable remote control device 253. While the wearable remote control device 253 is discussed with reference to a law enforcement officer, such a device can also be used by emergency personnel, or with other individuals not associated with either law enforcement or emergency personnel.

The camera 250 may be carried by an individual user and may be used to capture images. Alternatively, the camera 250 may be attached to the vehicle and may capture images inside or outside of the vehicle. In either case, the camera 250 may transmit the images to the mobile apparatus 100, which may store the images and/or relay the images to one or more remote databases or servers using one or more of the long-range transceivers 120. In addition, the mobile apparatus may store and retain the images in storage device 130. The "store and forward" process reduces the chance of loss of the images and maintains high availability of the images to the mobile apparatus 100 even in the event of a network failure or outage.

The biometric device 255 may scan or otherwise monitor biometric information from an individual. For example, the biometric device 255 may receive a fingerprint or other biometric from the individual, which may be stored in the storage device 135, received and processed by the processor device 105, and/or transmitted to a remote database or server using one or more of the long-range transceivers 120. Similarly, the barcode scanner 260 may scan a barcode included on a product for sale within the vehicle, such as a taxi-cab, or other barcodes located on containers such as luggage or packages, people, and/or other vehicles. The barcodes may be located on packages that are being shipped by a delivery truck, for example, and may be scanned using the barcode scanner 260. The RFID device 280 may wirelessly sense a signal and/or information associated with luggage, people, and/or other vehicles. As with the biometrics, the scanned barcodes and RFID signals may be stored in the storage device 135, processed by the processor device 105, and/or transmitted to a remote database or server using one or more of the long-range transceivers 120. The "store and forward" process reduces the chance of loss of the biometric information or barcode information, and maintains high availability of such information to the mobile apparatus 100 even in the event of a network failure or outage.

The smart card interface 267 may read information from a smart card such as a compact flash card, or write information thereto. The smart card can include, for example, information such as images, applications, and/or other files, which may be uploaded to the mobile apparatus 100 and stored by the storage device 135 and/or processed by the processor device 105.

The vehicle power train control modules (PCMs) 275 can provide information about the vehicle to the mobile in-vehicle communication and routing apparatus 100, which may then be processed by the processor device 105, stored in the storage device 135, and/or transmitted to a remote database or server. Alternatively, information can be transmitted from the mobile apparatus 100 to the vehicle power train control modules 275 to control the vehicle, such as by controlling the fuel, ignition, idle speed, and/or other parameters of an internal combustion engine or electric vehicle system, using the processor device 105 and/or at least one of the long-range transceivers 120.

In some embodiments, the processor device 105 receives information about the vehicle from the vehicle power train control modules 275, using a wired or short-range wireless connection. The information about the vehicle can include, for example, a status of the fuel system, ignition, idle speed, and so forth, and then in response to that information, adjust or control the vehicle such as by controlling the fuel, ignition, idle speed, and so forth. In some embodiments, status information is gathered and transmitted to the remote database or server, processed at the remote database or server, and then in response, instructions can be received by the processor device 105 of the mobile apparatus 100 from the remote database or server regarding how to adjust or control the vehicle settings using the vehicle power train control modules 275. One or more PCM setting for one or more vehicle power train control modules can then be adjusted accordingly using the processor device 105.

The mobile device 100 may also communicate with various interfaces 274 to the vehicle's electronic controls, relays, sensors, or diagnostics systems. For example, on-board diagnostics (OBD) ports in the vehicle can transmit diagnostics or emissions information to the processor device 105 via a wired or wireless connection 290. The processor device 105 can process and/or store such information in the storage device 135, or transmit the information to one or more remote databases or servers. In some embodiments, the processor device 105 receives and processes information about the vehicle braking system, engine status information, air conditioner unit information, heating system, oxygen sensors, throttle position sensors, and/or engine service information, among other types of vehicle information. In this manner, the mobile device 100 can identify and diagnose vehicle maintenance issues at an early stage. Such early detection capability reduces fleet down-time, maintenance costs, and fuel consumption. Moreover, high-risk driving behaviors can be identified and mitigated.

In some embodiments, the diagnostics or emissions information is gathered and transmitted to the one or more remote database or servers, processed at the remote database or server, and then in response, instructions can be received by the mobile apparatus 100 from the remote database or server regarding how to adjust or control the vehicle settings using the interfaces 274 to improve the operation of the vehicle braking system, engine status information, air conditioner unit information, heating system, oxygen sensors, throttle position sensors, and/or engine service information, among other types of vehicle information. The adjustments can be made based on the instructions using the processor device 105 and/or the interfaces 274.

The vehicle information, such as the diagnostics or emissions information, may be transmitted using a Controller-area network (CAN Bus) or J-Bus protocols. The processor device 105 can also control door locks, engine shutdown or startup, window positions, and other operable features of a vehicle using one or more of the interfaces 274. In this manner, the mobile device 100 can sense and control various aspects of the status and operation of the vehicle.

The medical and/or health diagnostic or monitoring device 277 can receive inputs from a user within the vehicle, or around the vicinity of the vehicle. For example, persons with diabetes can check their blood sugar concentration or glucose levels using the medical and/or health diagnostic or monitoring device 277, which they may choose to transmit to a remotely located computer or database. In another embodiment, users can check their heart rate or blood pressure using the medical and/or health diagnostic or monitoring device 277. The medical and/or health diagnostic or monitoring device 277 can include a defibrillator, or other medical device, used by medical or emergency personnel to revive or otherwise treat a person in or around the vehicle. Information recorded by the defibrillator, or other medical device, can be saved to the storage device 135 and/or transmitted via one or more of the long-range transceivers 120 to a remote medical center or remote database. More generally, taxi-cab passengers or other consumers may use the medical and/or health diagnostic or monitoring device 277 to check blood pressure or heart rate while travelling to their desired location, and may have the information transmitted to a remote computer or database for later retrieval.

Although the medical and/or health information can use the "store and forward" mode and/or process as similarly described above, in some embodiments, a "forward only" mode and/or process can be selected and used so that the medical and/or health information is not stored locally in the mobile device 100, thereby preserving the private nature of the information, while still quickly delivering the information over the network to persons or entities with a need to know the information.

Figure 3:
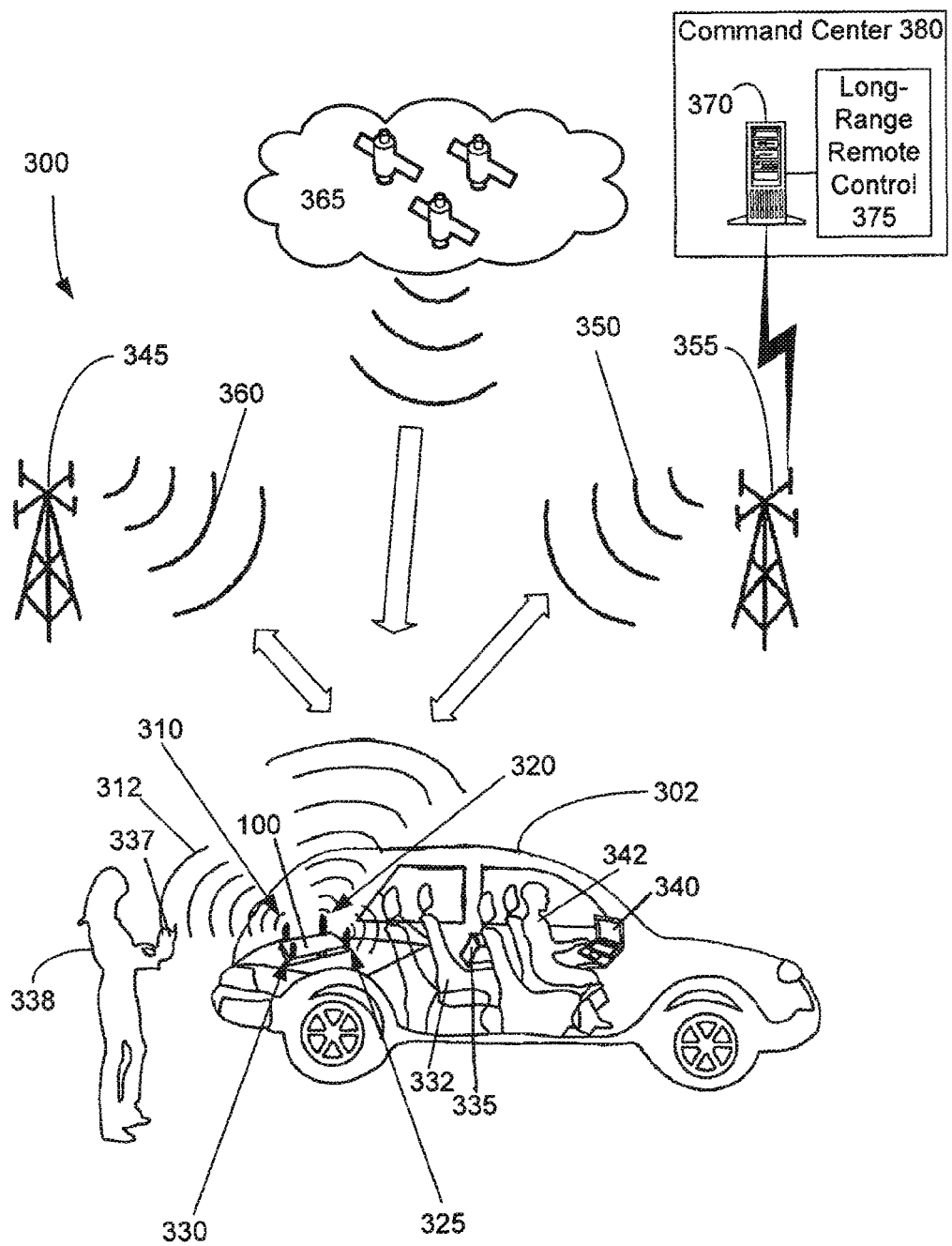
FIG. 3 shows an example system including the mobile in-vehicle communication and routing apparatus of FIG. 1.

FIG. 3 shows an example system 300 including the mobile in-vehicle communication and routing apparatus 100 of FIG. 1. The system 300 includes a vehicle 302, remote towers 345 and 355, and GPS satellites 365. The remote towers 345 and 355 may be cellular towers operating in association with a cellular network, as previously described.

The vehicle 302 includes therein, or attached thereto, a mobile in-vehicle communication and routing apparatus 100. The mobile in-vehicle communication and routing apparatus 100 may include one or more antennas such as 310, 320, 325, and 330, which may be operatively associated with the long-range wireless transceivers 120 and/or the short-range wireless transceivers 145, 150, 155, or 160. For example, as shown in FIG. 3, antenna 310 may transmit and receive signals such as 312 to and from an external device 337 held by user 338 located outside of, but proximally located to, the vehicle 302. In addition, antenna 320 may transmit and receive signals such as 360 and 350 to and from one or more remote towers such as 345 or 355.

Geographic positioning information can be transmitted by satellites 365 and received by antenna 330. Antenna 325 can be used to transmit or receive information to and from external device 335 and/or external device 340. The term "external" in this context means external relative to the mobile device 100. For example, a passenger sitting in location 332 in the vehicle 302 may interact with external device 335, which may be wired or wirelessly coupled to the mobile apparatus 100. Similarly, a driver 342 in the vehicle 302 may interact with external device 335, which may be wired or wirelessly coupled to the mobile apparatus 100.

Although multiple antennas are described as being associated with the mobile apparatus 100, it should be understood that a single antenna might be used; or one antenna can be used for all short-range communications, while another antenna is used for all long-range communications. In this manner, information can be communicated between users (e.g., 342) located within the vehicle 302 and the mobile apparatus 100, or between users (e.g., 338) proximally located about the vehicle 302 and the mobile apparatus 100, or between users (e.g., 342) located within the vehicle 302 and users (e.g., 338) proximally located about the vehicle 302.

Information can also be communicated between the mobile apparatus 100 and one or more remote towers (e.g., 345 and 355), one or more remote databases or servers 370, and/or long-range remote control device 375. The processor device 105 of the mobile apparatus 100 can be remotely managed or monitored by persons using the long-range remote control device 375 not located in the vehicle or about the vehicle (i.e., by persons located remotely from the vehicle). Such remote management capability simplifies operation and maintenance of the mobile apparatus 100. In addition, any of the remote control features discussed above with reference to the human-wearable remote control device 253 can also apply to the long-range remote control device 375 so that, for example, the long-range remote control device can operate the lights, still-image cameras, video cameras, car ignition system, vehicle heating and/or air-conditioner system, etc., can be controlled using the long-range remote control device 375.

In this manner, the mobile apparatus 100 provides short-range and long-range communication and computing services, and routes the information between the services in a cohesive, automated, and compact apparatus. Command centers such as command center 380 or other remote individuals can access information from the mobile apparatus 100, thereby providing real-time visibility into fleet status, and/or facilitating dispatching of fleet vehicles. The command center 380 can be operatively associated with each of the vehicles, and can communicate with the mobile apparatus 100 of each vehicle, and with any of the external devices such as 335, 340, and 337. The mobile apparatus 100 provides a versatile and user-friendly interface, which can assist taxi-cab drivers, law enforcement, emergency personnel, trucking companies, or any mobile vehicle, in easily communicating between vehicles and remote command centers. Persons or devices that are within the vehicle, or proximally located to the vehicle, can have their communicating or processing needs satisfied. Various devices, as described above, can be operatively coupled to the mobile apparatus 100 and used by persons within the vehicle or located about the vehicle.

Figure 4:
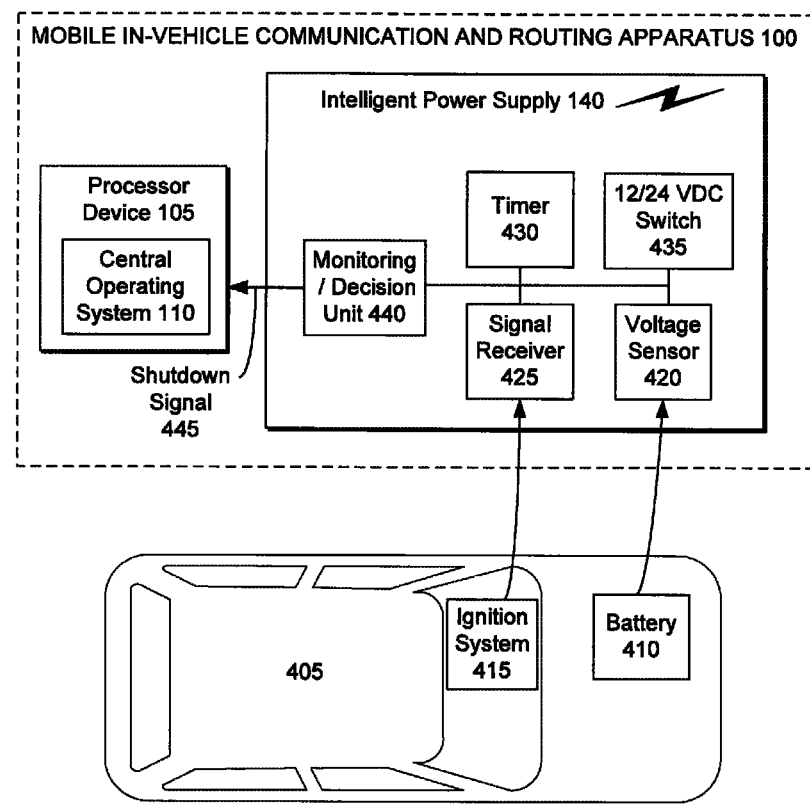
FIG. 4 shows a block diagram including various aspects of the intelligent power supply included in the mobile in-vehicle communication and routing apparatus of FIG. 1.

FIG. 4 shows a block diagram including various aspects of the intelligent power supply 140 included in the mobile in-vehicle communication and routing apparatus 100 of FIG. 1. The intelligent power supply 140 receives power from battery 410, and may include a voltage sensor 420, a signal receiver 425, a timer 430, a 12/24 VDC switch 435, and a monitoring and/or decision unit 440. A vehicle such as 405 has attached thereto, or included therein, the mobile apparatus 100. An ignition system 415 within the vehicle 405 transmits an ignition signal, preferably an ignition "off" signal to the receiver 425. Such ignition "off" signal indicates that the vehicle 405 is in an "off" state, or in other words, the battery 410 of the vehicle 405 is no longer receiving a charge from the vehicle 405. When the receiver 425 receives the ignition signal, the timer 430 begins to countdown from a predefined value. The predefined value can be a factory-default value ranging, for example, between 2 minutes and 2 hours, or any other suitable value. Alternatively, the predefined value is configurable by a user of the mobile apparatus 100. The monitoring and/or decision unit 440 monitors the timer 430 and when the timer completes the countdown, a shutdown signal 445 is transmitted to the processor device 105 and the central operating system 110 initiates a soft (i.e., controlled) shutdown of the mobile in-vehicle communication and routing apparatus 100.

When the timer 430 is counting down, the voltage sensor 420 monitors a low-battery condition of the vehicle battery 410. For example, if the voltage sensor 420 detects that a voltage of the battery 410 drops below or is below a predefined threshold, the monitoring and/or decision unit 440 can preempt the timer 430 and immediately transmit the shutdown signal 445. Since the mobile device 100 may generally be drawing energy from the battery 410 when turned on, the power down preemption technique prevents the battery 410 of the vehicle 405 from completely draining or otherwise damaging the battery or vehicle, and ensures that the vehicle can be later started. Although shown in FIG. 4 as being directly connected to the battery 410, the voltage sensor 420 need not be directly connected thereto. For example, the voltage sensor 420 can sense the voltage of the battery 410 through a wired system or device that is coupled to the battery 410.

The predefined voltage threshold can be determined based at least in part on the 12/24 VDC switch 435 setting. In other words, some vehicle batteries operate or are rated at 12 VDC, while other vehicles operate or are rated at 24 VDC. The switch 435 can be a dip-switch, and is configurable by a user of the mobile apparatus 100 to either the 12 VDC or 24 VDC setting. The predefined threshold is less than 12 VDC in the case of the 12 VDC setting, and is less than 24 VDC in the case of the 24 VDC setting. For instance, the predefined threshold can be, for example, between 10 VDC and 11.9 VDC in the case of a 12 VDC rated battery system, or any other suitable value that is generally less than 12 VDC. Similarly, the predefined threshold can be, for example, between 22 VDC and 23.9 VDC in the case of a 24 VDC rated battery system, or any other suitable value that is generally less than 24 VDC. When the predefined threshold voltage is crossed or otherwise detected by the voltage sensor 420, the soft shutdown of the mobile apparatus 100 is initiated, irrespective of whether the timer 430 has completed the countdown.

For example, if the predefined timer value is set to 30 minutes, the shutdown signal 445 will be transmitted after the 30 minutes have expired. However, if during the 30 minutes the voltage sensor 420 detects that the predefined voltage threshold of the battery 410 has been crossed, the shutdown signal 445 will be transmitted before the 30 minutes have expired. In this manner, multiple safeguards prevent the mobile in-vehicle apparatus 100 from experiencing hard crashes, and prevent the battery 410 from undesirable draining.

Figure 5:
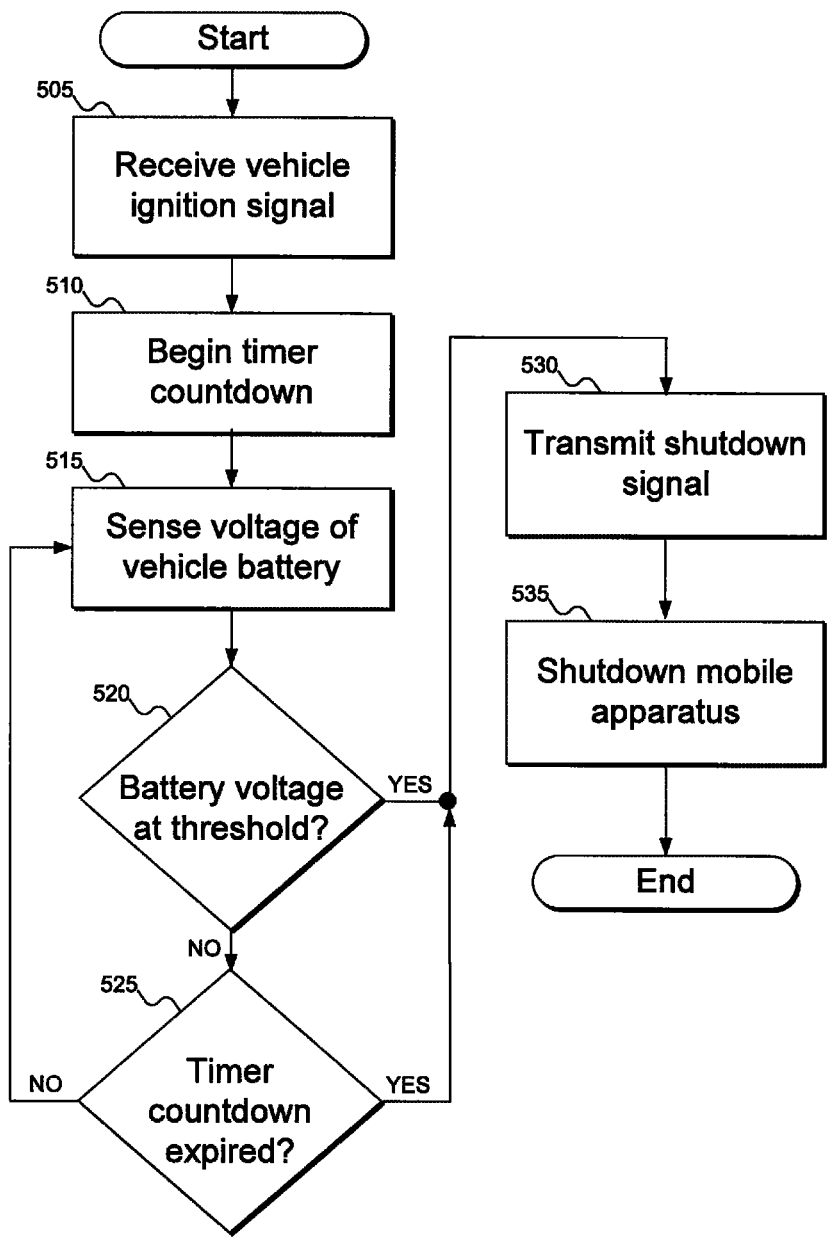
FIG. 5 shows a flow diagram of a technique for monitoring a vehicle battery and initiating a controlled shutdown of the mobile in-vehicle communication and routing apparatus of FIG. 1.

FIG. 5 shows a flow diagram of a technique for monitoring a vehicle battery and initiating a controlled shutdown of the mobile in-vehicle communication and routing apparatus of FIG. 1. At 505, a vehicle ignition signal is received by the intelligent power supply. Upon receiving the vehicle ignition signal, the timer (e.g., 430) begins a countdown from a predefined value. The voltage sensor 420 senses a voltage of the vehicle battery 410 at 515. At 520, a determination is made whether a battery voltage is at a threshold, or has otherwise crossed a predefined voltage threshold. If yes, the flow proceeds to 530 and a shutdown signal is transmitted to initiate a soft (i.e., controlled) shutdown of the mobile apparatus 100. If no, the flow proceeds to 525 and a determination is made whether the timer countdown has expired. If yes, the flow proceeds to 530. Otherwise, the flow returns to 515 and the voltage of the vehicle battery is again sensed. In any case, the flow eventually proceeds to 535 and the mobile apparatus 100 is shut down in a controlled manner, thereby preserving the charge within the vehicle battery 410, but at the same time, allowing one or more users to continue to use the mobile apparatus 100 even after the vehicle 405 has been turned off.

The following discussion is intended to provide a brief, general description of a suitable machine or machines in which certain aspects of the invention can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciated that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the invention can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the invention with reference to illustrated embodiments, it will be recognized that the illustrated embodiments can be modified in arrangement and detail without departing from such principles, and can be combined in any desired manner. And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms can reference the same or different embodiments that are combinable into other embodiments.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

The invention claimed is:

1. A mobile apparatus attachable to a vehicle, the apparatus comprising:
a plurality of long-range transceivers communicatively coupled with one or more databases located remotely from the vehicle; and
a plurality of short-range transceivers communicatively coupled with one or more devices external to the mobile apparatus and proximally located to the vehicle;
a processor device communicatively coupled with the one or more databases located remotely from the vehicle via one of the plurality of long-range transceivers;
a storage device; and
an intelligent power supply structured to monitor a battery condition of the vehicle;
wherein the processor device is structured to:
receive information about the vehicle from one or more power train control modules (PCMs);
transmit the PCM information to the one or more databases located remotely from the vehicle via one of the plurality of long-range transceivers;
receive instructions from the one or more databases located remotely from the vehicle via one of the plurality of long-range transceivers; and
adjust one or more settings of the one or more PCMs in accordance with the instructions;
wherein the intelligent power supply is structured to transmit a shutdown signal to the mobile apparatus responsive to at least one of a user configurable timer countdown and a voltage threshold of a vehicle battery;
wherein the intelligent power supply further comprises:
a timer configured to begin the timer countdown responsive to receiving an ignition off signal from a vehicle ignition system;
a voltage sensor configured to sense when a voltage of the vehicle battery drops below the voltage threshold; and
a monitoring and decision unit configured to make an initial voltage threshold determination after the beginning of the timer countdown, whether the voltage of the vehicle battery has dropped below the voltage threshold, wherein the initial voltage threshold determination is made prior to an initial timer countdown determination of whether the timer countdown has expired;
wherein in response to determining that the voltage of the vehicle battery has dropped below the voltage threshold, the monitoring and decision unit is configured to transmit the shutdown signal to initiate a soft shutdown of the mobile apparatus;
wherein the monitoring and decision unit is further configured to make the initial timer countdown determination, after the initial voltage threshold determination, whether the timer countdown has expired;
wherein in response to determining that the timer countdown has expired, the monitoring and decision unit is configured to transmit the shutdown signal to initiate the soft shutdown of the mobile apparatus; and
wherein the monitoring and decision unit is configured to repeat the voltage threshold determination directly followed by the timer countdown determination until the shutdown signal is transmitted.

2. The mobile apparatus of claim 1, wherein:
the processor device is structured to transmit and receive information to and from the devices external to the mobile apparatus via at least one of the plurality of short-range transceivers, and
the processor device is structured to transmit and receive the information to and from the one or more databases located remotely from the vehicle via at least one of the plurality of long-range transceivers.

3. The mobile apparatus of claim 1, wherein the monitoring and decision unit is configured to transmit the shutdown signal when the timer completes the countdown.

4. The mobile apparatus of claim 3, wherein the monitoring and decision unit is configured to preempt the timer countdown and immediately transmit the shutdown signal when the voltage sensor detects that the voltage of the vehicle battery drops below the voltage threshold.

5. The mobile apparatus of claim 1, wherein:
the processor device includes a central operating system to receive the shutdown signal from the monitoring and decision unit, and to initiate the soft shutdown of the mobile apparatus including shutdown of the processor device, the timer, the voltage sensor, and the monitoring and decision unit responsive to the shutdown signal.

6. The mobile apparatus of claim 1, wherein the threshold voltage is less than 12 VDC for vehicle battery systems rated at 12 VDC, and wherein the threshold voltage is less than 24 VDC for vehicle battery systems rated at 24 VDC.

7. The mobile apparatus of claim 1, further comprising:
a biometric device structured to receive biometric information from an individual;

wherein the processor device is structured to:
  receive and process the biometric information;
  store the biometric information in the storage device; and
  transmit the biometric information to the one or more remote databases via at least one of the plurality of long-range transceivers.

8. The mobile apparatus of claim 1, further comprising:
a barcode scanner structured to scan barcode information from one or more containers;
wherein the processor device is structured to:
  receive and process the barcode information;
  store the barcode information in the storage device; and
  transmit the barcode information to the one or more remote databases via at least one of the plurality of long-range transceivers.

9. The mobile apparatus of claim 1, wherein:
the processor device is structured to:
  receive on-board diagnostic (OBD) information about the vehicle from one or more OBD ports in the vehicle;
  transmit the OBD information to the one or more databases located remotely from the vehicle via at least one of the plurality of long-range transceivers;
  receive instructions from the one or more databases located remotely from the vehicle via at least one of the plurality of long-range transceivers, wherein the instructions are based at least on the OBD information transmitted to the one or more remotely located databases; and
  adjust one or more vehicle settings in accordance with the instructions.

10. The mobile apparatus of claim 1, further comprising:
a global positioning system (GPS) configured to receive positioning information of the mobile apparatus;
a barcode scanner structured to scan barcode information from one or more containers;
wherein the processor device is structured to:
  receive and process the barcode information;
  timestamp the positioning information;
  store the barcode information and the timestamped positioning information in the storage device; and
  transmit the barcode information and the timestamped positioning information to the one or more remote databases via at least one of the plurality of long-range transceivers.

11. The mobile apparatus of claim 1, further comprising:
a medical diagnostic monitoring device configured to receive medical diagnostic information from one or more individuals proximately located to the vehicle;
a global positioning system (GPS) configured to receive positioning information of the mobile apparatus;
wherein the processor device is structured to:
  receive and process the medical diagnostic information;
  timestamp the positioning information;
  in a store and forward mode, store the medical diagnostic information and the timestamped positioning information in the storage device, and transmit the medical diagnostic information and the timestamped positioning information to the one or more remote databases via at least one of the plurality of long-range transceivers; and
  in a forward only mode, not store the medical diagnostic information in the storage device, and transmit the medical diagnostic information and the timestamped positioning information to the one or more remote databases via at least one of the plurality of long-range transceivers.

12. The mobile apparatus of claim 1, wherein:
the PCM information includes a status of a fuel system of the vehicle, information about an ignition system of the vehicle, and information about an idle speed of the vehicle;
the processor device is configured to transmit, to the one or more databases located remotely from the vehicle, via at least one of the plurality of long-range transceivers, the status of the fuel system of the vehicle, the information about the ignition system of the vehicle, and the information about the idle speed of the vehicle; and
the processor device is configured to receive, from the one or more databases located remotely from the vehicle, via at least one of the plurality of long-range transceivers, an instruction to control the fuel system of the vehicle, an instruction to control the ignition system of the vehicle, and an instruction to control the idle speed of the vehicle.

13. The mobile apparatus of claim 9, wherein the instructions received from the one or more databases located remotely from the vehicle further comprise:
  an instruction to improve an operation of a braking system of the vehicle, an instruction to operate one or more lights of the vehicle, an instruction to operate one or more still-image cameras associated with the vehicle, an instruction to operate one or more video cameras associated with the vehicle, an instruction to operate an ignition system of the vehicle, an instruction to operate a heating system of the vehicle, and an instruction to operate the air-conditioner system of the vehicle.

14. The mobile apparatus of claim 9, wherein the instructions received from the one or more databases located remotely from the vehicle further comprise:
  an instruction to improve an operation of one or more oxygen sensors of the vehicle; and
  an instruction to improve an operation of one or more throttle position sensors of the vehicle.

15. A mobile apparatus attachable to a vehicle, the apparatus comprising:
  a plurality of long-range transceivers communicatively coupled with one or more databases located remotely from the vehicle; and
  a plurality of short-range transceivers communicatively coupled with one or more devices external to the mobile apparatus and proximately located to the vehicle;
  a processor device communicatively coupled with the one or more databases located remotely from the vehicle via one of the plurality of long-range transceivers; and
  a storage device;
  wherein the processor device is structured to:
    receive information about the vehicle from one or more power train control modules (PCMs);
    transmit the PCM information to the one or more databases located remotely from the vehicle via one of the plurality of long-range transceivers;
    receive instructions from the one or more databases located remotely from the vehicle via one of the plurality of long-range transceivers;
    adjust one or more settings of the one or more PCMs in accordance with the instructions;
    receive on-board diagnostic (OBD) information about the vehicle from one or more OBD ports in the vehicle;

transmit the OBD information to the one or more databases located remotely from the vehicle via at least one of the plurality of long-range transceivers;
receive instructions from the one or more databases located remotely from the vehicle via at least one of the plurality of long-range transceivers, wherein the instructions are based at least on the OBD information transmitted to the one or more remotely located databases; and
adjust one or more vehicle settings in accordance with the instructions;
wherein the instructions received from the one or more databases located remotely from the vehicle further comprise:
an instruction to improve an operation of a braking system of the vehicle, an instruction to operate one or more lights of the vehicle, an instruction to operate one or more still-image cameras associated with the vehicle, an instruction to operate one or more video cameras associated with the vehicle, an instruction to operate an ignition system of the vehicle, an instruction to operate a heating system of the vehicle, and an instruction to operate the air-conditioner system of the vehicle.

16. The mobile apparatus of claim 15, wherein:
the processor device is structured to transmit and receive information to and from the devices external to the mobile apparatus via at least one of the plurality of short-range transceivers, and
the processor device is structured to transmit and receive the information to and from the one or more databases located remotely from the vehicle via at least one of the plurality of long-range transceivers.

17. The mobile apparatus of claim 15, further comprising:
an intelligent power supply structured to monitor a battery condition of the vehicle.

18. The mobile apparatus of claim 17, wherein the intelligent power supply is structured to transmit a shutdown signal to the mobile apparatus responsive to at least one of a user configurable timer countdown and a voltage threshold of a vehicle battery.

19. The mobile apparatus of claim 15, further comprising:
a biometric device structured to receive biometric information from an individual;
wherein the processor device is structured to:
receive and process the biometric information;
store the biometric information in the storage device; and
transmit the biometric information to the one or more remote databases via at least one of the plurality of long-range transceivers.

20. The mobile apparatus of claim 15, further comprising:
a barcode scanner structured to scan barcode information from one or more containers;
wherein the processor device is structured to:
receive and process the barcode information;
store the barcode information in the storage device; and
transmit the barcode information to the one or more remote databases via at least one of the plurality of long-range transceivers.

21. The mobile apparatus of claim 15, further comprising:
a global positioning system (GPS) configured to receive positioning information of the mobile apparatus;
a barcode scanner structured to scan barcode information from one or more containers;
wherein the processor device is structured to:
receive and process the barcode information;
timestamp the positioning information;
store the barcode information and the timestamped positioning information in the storage device; and
transmit the barcode information and the timestamped positioning information to the one or more remote databases via at least one of the plurality of long-range transceivers.

22. The mobile apparatus of claim 15, further comprising:
a medical diagnostic monitoring device configured to receive medical diagnostic information from one or more individuals proximately located to the vehicle;
a global positioning system (GPS) configured to receive positioning information of the mobile apparatus;
wherein the processor device is structured to:
receive and process the medical diagnostic information;
timestamp the positioning information;
in a store and forward mode, store the medical diagnostic information and the timestamped positioning information in the storage device, and transmit the medical diagnostic information and the timestamped positioning information to the one or more remote databases via at least one of the plurality of long-range transceivers; and
in a forward only mode, not store the medical diagnostic information in the storage device, and transmit the medical diagnostic information and the timestamped positioning information to the one or more remote databases via at least one of the plurality of long-range transceivers.

23. The mobile apparatus of claim 15, wherein:
the PCM information includes a status of a fuel system of the vehicle, information about an ignition system of the vehicle, and information about an idle speed of the vehicle;
the processor device is configured to transmit, to the one or more databases located remotely from the vehicle, via at least one of the plurality of long-range transceivers, the status of the fuel system of the vehicle, the information about the ignition system of the vehicle, and the information about the idle speed of the vehicle; and
the processor device is configured to receive, from the one or more databases located remotely from the vehicle, via at least one of the plurality of long-range transceivers, an instruction to control the fuel system of the vehicle, an instruction to control the ignition system of the vehicle, and an instruction to control the idle speed of the vehicle.

24. A mobile apparatus attachable to a vehicle, the apparatus comprising:
a plurality of long-range transceivers communicatively coupled with one or more databases located remotely from the vehicle; and
a plurality of short-range transceivers communicatively coupled with one or more devices external to the mobile apparatus and proximally located to the vehicle;
a processor device communicatively coupled with the one or more databases located remotely from the vehicle via one of the plurality of long-range transceivers; and
a storage device;
wherein the processor device is structured to:
receive information about the vehicle from one or more power train control modules (PCMs);
transmit the PCM information to the one or more databases located remotely from the vehicle via one of the plurality of long-range transceivers;
receive instructions from the one or more databases located remotely from the vehicle via one of the plurality of long-range transceivers;
adjust one or more settings of the one or more PCMs in accordance with the instructions;

receive on-board diagnostic (OBD) information about the vehicle from one or more OBD ports in the vehicle;

transmit the OBD information to the one or more databases located remotely from the vehicle via at least one of the plurality of long-range transceivers;

receive instructions from the one or more databases located remotely from the vehicle via at least one of the plurality of long-range transceivers, wherein the instructions are based at least on the OBD information transmitted to the one or more remotely located databases; and adjust one or more vehicle settings in accordance with the instructions;

wherein the instructions received from the one or more databases located remotely from the vehicle further comprise:

an instruction to improve an operation of one or more oxygen sensors of the vehicle; and an instruction to improve an operation of one or more throttle position sensors of the vehicle.

25. The mobile apparatus of claim 24, wherein:

the processor device is structured to transmit and receive information to and from the devices external to the mobile apparatus via at least one of the plurality of short-range transceivers, and the processor device is structured to transmit and receive the information to and from the one or more databases located remotely from the vehicle via at least one of the plurality of long-range transceivers.

26. The mobile apparatus of claim 24, further comprising:

an intelligent power supply structured to monitor a battery condition of the vehicle.

27. The mobile apparatus of claim 26, wherein the intelligent power supply is structured to transmit a shutdown signal to the mobile apparatus responsive to at least one of a user configurable timer countdown and a voltage threshold of a vehicle battery.

28. The mobile apparatus of claim 24, further comprising:

a biometric device structured to receive biometric information from an individual;

wherein the processor device is structured to:

receive and process the biometric information;

store the biometric information in the storage device; and transmit the biometric information to the one or more remote databases via at least one of the plurality of long-range transceivers.

29. The mobile apparatus of claim 24, further comprising:

a barcode scanner structured to scan barcode information from one or more containers;

wherein the processor device is structured to:

receive and process the barcode information;

store the barcode information in the storage device; and transmit the barcode information to the one or more remote databases via at least one of the plurality of long-range transceivers.

30. The mobile apparatus of claim 24, further comprising:

a global positioning system (GPS) configured to receive positioning information of the mobile apparatus;

a barcode scanner structured to scan barcode information from one or more containers;

wherein the processor device is structured to:

receive and process the barcode information;

timestamp the positioning information;

store the barcode information and the timestamped positioning information in the storage device; and transmit the barcode information and the timestamped positioning information to the one or more remote databases via at least one of the plurality of long-range transceivers.

31. The mobile apparatus of claim 24, further comprising:

a medical diagnostic monitoring device configured to receive medical diagnostic information from one or more individuals proximately located to the vehicle;

a global positioning system (GPS) configured to receive positioning information of the mobile apparatus;

wherein the processor device is structured to:

receive and process the medical diagnostic information;

timestamp the positioning information;

in a store and forward mode, store the medical diagnostic information and the timestamped positioning information in the storage device, and transmit the medical diagnostic information and the timestamped positioning information to the one or more remote databases via at least one of the plurality of long-range transceivers; and in a forward only mode, not store the medical diagnostic information in the storage device, and transmit the medical diagnostic information and the timestamped positioning information to the one or more remote databases via at least one of the plurality of long-range transceivers.

32. The mobile apparatus of claim 24, wherein:

the PCM information includes a status of a fuel system of the vehicle, information about an ignition system of the vehicle, and information about an idle speed of the vehicle;

the processor device is configured to transmit, to the one or more databases located remotely from the vehicle, via at least one of the plurality of long-range transceivers, the status of the fuel system of the vehicle, the information about the ignition system of the vehicle, and the information about the idle speed of the vehicle; and the processor device is configured to receive, from the one or more databases located remotely from the vehicle, via at least one of the plurality of long-range transceivers, an instruction to control the fuel system of the vehicle, an instruction to control the ignition system of the vehicle, and an instruction to control the idle speed of the vehicle.

* * * * *

UNITED STATES PATENT AND TRADEMARK OFFICE
CERTIFICATE OF CORRECTION

| | | |
|---|---|---|
| PATENT NO. | : 8,670,897 B1 | Page 1 of 1 |
| APPLICATION NO. | : 12/956293 | |
| DATED | : March 11, 2014 | |
| INVENTOR(S) | : Robert E. Ralston | |

It is certified that error appears in the above-identified patent and that said Letters Patent is hereby corrected as shown below:

Item (75) the surname of the inventor as printed on the title page of the patent should be changed from "Ralson" to --Ralston--.

Signed and Sealed this
Twentieth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,670,897 B1 | Page 1 of 1 |
| APPLICATION NO. | : 12/956293 | |
| DATED | : March 11, 2014 | |
| INVENTOR(S) | : Robert E. Ralston | |

It is certified that error appears in the above-identified patent and that said Letters Patent is hereby corrected as shown below:

Title page, item (12), delete "Ralson" and insert --Ralston--.

Item (75) the surname of the inventor as printed on the title page of the patent should be changed from "Ralson" to --Ralston--.

This certificate supersedes the Certificate of Correction issued May 20, 2014.

Signed and Sealed this
Tenth Day of June, 2014

Michelle K. Lee
*Deputy Director of the United States Patent and Trademark Office*